United States Patent
Daniels et al.

(10) Patent No.: US 6,319,239 B1
(45) Date of Patent: *Nov. 20, 2001

(54) ABSORBENT ARTICLE HAVING IMPROVED INTEGRITY AND ACQUISITION

(75) Inventors: Dean Jeffrey Daniels; Tana Marie Kirkbride, both of Cincinnati; Stephanie Tych Craig, Loveland; Anne Holland Bruce, Cincinnati, all of OH (US)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/074,909

(22) Filed: May 8, 1998

Related U.S. Application Data

(63) Continuation-in-part of application No. PCT/US96/20873, filed on Dec. 20, 1996.

(51) Int. Cl.[7] ..................................................... A61F 13/15
(52) U.S. Cl. ...................................... 604/385.01; 604/378
(58) Field of Search ................................ 604/385.2, 378, 604/374, 368, 385.01, 367, 382, 383; 428/137, 131

(56) References Cited

U.S. PATENT DOCUMENTS

| | | |
|---|---|---|
| D. 254,099 | 2/1980 | Richards . |
| D. 272,190 | 1/1984 | Sneider . |
| D. 293,606 | 1/1988 | James . |
| D. 362,967 | 10/1995 | Rothwell et al. . |
| D. 367,764 | 3/1996 | Makoui et al. . |
| D. 367,765 | 3/1996 | Makoui et al. . |

(List continued on next page.)

FOREIGN PATENT DOCUMENTS

| | | |
|---|---|---|
| 32 05 931 A | 9/1983 | (DE) . |
| 0 621 082 A | 10/1994 | (EP) . |
| 0 685 214 A2 | 12/1995 | (EP) . |
| 2288412 A | 4/1994 | (GB) . |
| WO 93/11725 | 6/1993 | (WO) . |
| WO 93/11726 | 6/1993 | (WO) . |
| WO 95/07674 | 3/1995 | (WO) . |
| WO 95/17867 | 7/1995 | (WO) . |
| WO 96/00545 | 1/1996 | (WO) . |
| WO 96/00625 | 1/1996 | (WO) . |
| WO 98/27904 | 7/1998 | (WO) . |
| WO 99/58092 | * 11/1999 | (WO) . |

OTHER PUBLICATIONS

Sample of Bounty paper towel.*

*Primary Examiner*—Dennis Ruhl
(74) *Attorney, Agent, or Firm*—Matthew O. Fitzpatrick; Jeffrey V. Bamber

(57) ABSTRACT

Absorbent articles such as sanitary napkins, panty liners, adult incontinence devices, and the like, that have components that are bonded for improved integrity and an unbonded window on their body-facing side for improved acquisition are disclosed. The absorbent articles comprise a topsheet that is fused to an underlying liquid pervious or absorbent layer at a plurality of individual bonded areas. The absorbent articles have an unbonded window that is substantially free of bonded areas, which is surrounded by regions of the absorbent article that contain bonded areas.

20 Claims, 2 Drawing Sheets

U.S. PATENT DOCUMENTS

| | | |
|---|---|---|
| D. 367,766 | 3/1996 | Makoui et al. . |
| D. 372,589 | 8/1996 | Burgess et al. . |
| D. 399,310 | 10/1998 | Lynard et al. . |
| D. 399,953 | 10/1998 | Kollner . |
| D. 403,763 | 1/1999 | Lynard et al. . |
| D. 403,764 | 1/1999 | Lynard et al. . |
| D. 403,765 | 1/1999 | Lynard et al. . |
| 3,292,619 | 12/1966 | Egler . |
| 3,575,174 | 4/1971 | Mogor . |
| 3,903,890 | 9/1975 | Mesek et al. . |
| 4,059,114 | 11/1977 | Richards . |
| 4,184,498 | 1/1980 | Franco . |
| 4,315,507 | 2/1982 | Whitehead et al. . |
| 4,333,979 | 6/1982 | Sciaraffa et al. . |
| 4,397,644 * | 8/1983 | Matthews et al. .................. 604/378 |
| 4,443,512 | 4/1984 | Delvaux . |
| 4,505,705 | 3/1985 | Matthews et al. . |
| 4,624,666 | 11/1986 | DeRossett et al. . |
| 4,636,209 | 1/1987 | Lassen . |
| 4,655,759 | 4/1987 | Romans-Hess et al. . |
| 4,673,403 | 6/1987 | Lassen et al. . |
| 4,690,679 | 9/1987 | Mattingly, III et al. . |
| 4,726,976 | 2/1988 | Karami et al. . |
| 4,753,840 | 6/1988 | Van Gombel . |
| 4,778,460 | 10/1988 | Braun et al. . |
| 4,798,603 | 1/1989 | Meyer . |
| 4,823,783 | 4/1989 | Willhite, Jr. et al. . |
| 4,834,739 | 5/1989 | Linker, III et al. . |
| 4,844,965 | 7/1989 | Foxman . |
| 4,936,839 | 6/1990 | Molee et al. . |
| 5,091,240 | 2/1992 | Kajander et al. . |
| 5,128,082 | 7/1992 | Makoui . |
| 5,135,521 | 8/1992 | Luceri et al. . |
| 5,151,091 | 9/1992 | Glaug et al. . |
| 5,234,422 | 8/1993 | Sneller et al. . |
| 5,308,346 | 5/1994 | Sneller et al. . |
| 5,312,386 | 5/1994 | Correa et al. . |
| 5,360,419 * | 11/1994 | Chen et al. ..................... 604/374 |
| 5,378,528 | 1/1995 | Makoui . |
| 5,460,622 | 10/1995 | Dragoo et al. . |
| 5,558,655 * | 9/1996 | Jezzi et al. ..................... 604/378 |
| 5,591,149 * | 1/1997 | Cree et al. ..................... 604/378 |
| 5,603,707 * | 2/1997 | Trombetta et al. .............. 604/383 |
| 5,614,283 * | 3/1997 | Potnis et al. ..................... 428/131 |
| 5,643,238 * | 7/1997 | Baker .............................. 604/368 |
| 5,643,240 * | 7/1997 | Jackson et al. . |
| 5,647,863 * | 7/1997 | Hammons et al. .............. 604/378 |
| 5,713,881 * | 2/1998 | Rezai et al. ..................... 604/368 |
| 5,746,729 * | 5/1998 | Wada et al. ..................... 604/378 |
| 5,785,697 * | 7/1998 | Trombetta et al. .............. 604/378 |
| 5,788,684 * | 8/1998 | Abuto et al. ..................... 604/368 |
| 5,810,800 * | 9/1998 | Hunter et al. . |
| 5,817,394 * | 10/1998 | Alikhan et al. ................. 428/137 |
| 5,830,296 * | 11/1998 | Emenaker et al. .............. 156/219 |
| 5,925,026 * | 7/1999 | Arteman et al. ................. 604/383 |
| 5,986,167 * | 11/1999 | Arteman et al. ................. 604/380 |

* cited by examiner

ABSORBENT ARTICLE HAVING IMPROVED INTEGRITY AND ACQUISITION

This application is a continuation-in-part of Application No. PCT/US96/20873, filed on Dec. 20, 1996, pending.

FIELD OF THE INVENTION

The present invention relates to absorbent articles such as sanitary napkins, panty liners, adult incontinence devices, and the like. Still more particularly, the present invention concerns absorbent articles such as sanitary napkins, and the like that have improved integrity and an unbonded window on their body-facing side for improved acquisition.

BACKGROUND OF THE INVENTION

All manner and variety of absorbent articles configured for the absorption of body fluids such as menses, urine, and feces are, of course, well known. Absorbent articles are typically comprised of a number of layers of material. These generally include, from top to bottom, a liquid pervious layer, an absorbent layer, and a liquid impervious layer. Additional layers may also be interposed between any of these layers. Such additional layers may serve various different purposes.

The layers of absorbent articles are generally held together around their peripheries by some conventional means, such as adhesives, crimping, fusing, and other methods known in the art. The absorbent articles can have, and in many cases preferably will have, a liquid impermeable bond around their periphery. This will not interfere with the function of the absorbent article. However, it is frequently also desirable to bond the layers together at their faces. The attachment of the faces of these layers presents certain technical problems. This is particularly the case when it is desired to attach the upper liquid pervious layers and absorbent layers. The same means used for attaching the layers at their peripheries often cannot be used because they will tend to block the flow of liquids to the absorbent layers.

A number of attempts have been made to deal with this problem. These have included utilizing hot melt adhesives, and other non-water based adhesives. Such adhesives will be less likely to dissolve when contacted by body liquids. Other attempts have been directed at applying adhesives in very thin layers or in particular patterns to attempt to minimize the interference with the flow of liquids to the underlying layers. U.S. Pat. No. 4,573,986 issued to Minetola, et al. on Mar. 4, 1986 discloses one preferred way of applying adhesives. Although the application of adhesives in the manner described in the Minetola, et al. patent works quite well, the search for improved ways of securing the faces of the layers of absorbent products has continued.

The main reason for searching for improved ways of securing the faces of such layers is that in many cases, adhesives which initially function adequately, may eventually fail and cause the liquid pervious layers to become unattached. This problem is particularly apparent during prolonged use of an absorbent article. This problem is often heightened when the liquid pervious layer is an apertured plastic film. While apertured plastic films made according to the patents owned by the assignee of the present invention perform very well, certain problems can occur when they separate from their underlying layers. The plastic films are sufficiently thin that they can move well into the crevices of the wearer's body (such as the space between the wearer's buttocks) when they become unattached. This can be extremely uncomfortable and irritating. Because of its plastic composition, in some of these instances, the liquid pervious layer may even stick to the skin of the wearer. The adhesives may cause the film to present a sticky surface near the body of the wearer which may contribute to cause the liquid pervious layer to stick to the skin of the wearer.

The separation of the apertured film from the absorbent layers may also cause exudates to run off the top of the product along the longitudinal edges. Further, the exudates will not always penetrate the film if there is no longer an underlying absorbent layer in contact with the film for the exudates to wick into. This is particularly true in the case of thick pads having airfelt batts for their absorbent cores. The absorbent core of such thick pads tends to collapse and bunch (or gather in transversely) in the center of the product upon the first incidence of wetting. This gathering in, combined with the separation of the formed film, leaves the portion of the pad adjacent to its longitudinal edges without any underlying absorbent material, thereby increasing the possibility of runoff or leakage on top of the product along the longitudinal edges.

Several patents describe absorbent products having layers held together in alternative manners for various different purposes. Such efforts are described in U.S. Pat. Nos. 3,965,906 and 4,184,902 issued to Karami, U.S. Pat. No. 4,391,861 issued to Butterworth, et al., U.S. Pat. No. 4,397,644 issued to Matthews, et al., U.S. Pat. No. 4,475,911 issued to Gellert, U.S. Pat. No. 4,726,976 issued to Karami, et al., U.S. Pat. No. 4,752,349 issued to Gebel, U.S. Pat. No. 4,753,840 issued to Van Gompel, U.S. Pat. No. 4,823,783 issued to Willhite, Jr., et al., U.S. Pat. No. 4,844,965 issued to Foxman, and U.S. Pat. No. 4,908,026 issued to Sukiennik, et al. The majority of these patents, however, do not disclose fusing an apertured formed film on top of a liquid pervious material or an absorbent material, such as a nonwoven material. Such patents also do not disclose providing an absorbent article with an unbonded window on its body-facing side for improved acquisition.

Thus, a need exists for absorbent articles having improved bonding between their layers, particularly between the uppermost liquid pervious layers.

Therefore, it is an object of the present invention to provide absorbent articles having bonding between their layers, particularly the uppermost liquid pervious layers, that maintain sustained attachment even under prolonged use and are provided with more controlled resistance to undesirable bunching.

It is another object of the present invention to provide absorbent articles having liquid pervious layers that are bonded in a manner that does not interfere with the acquisition of liquids into the absorbent layer.

These and other objects of the present invention will be more readily apparent when considered in reference to the following description and when taken in conjunction with the accompanying drawings.

SUMMARY OF THE INVENTION

In accordance with the present invention, an absorbent article, such as a diaper, a sanitary napkin, a panty liner, an adult incontinence device, or the like is provided which has a bonded region to provide improved integrity and an unbonded window on its body-facing side for improved acquisition.

The absorbent article preferably comprises a sanitary napkin comprising a liquid pervious topsheet such as an apertured thermoplastic film, a liquid impervious backsheet that is either directly or indirectly joined to the topsheet, an absorbent core, and at least one acquisition component. The absorbent core is positioned between the topsheet and the backsheet. The acquisition component preferably comprises at least one layer of material, such as a fibrous nonwoven web. The acquisition component may either be a separate component positioned between the topsheet and the absorbent core, or it may comprise part of the topsheet or part of the absorbent core. The topsheet and the acquisition component are placed in a face-to-face relationship and the face of the topsheet is secured to the face of the acquisition component at discrete bonded areas. The discrete bonded areas are preferably formed by fusion bonds. The bonded areas are preferably spaced apart and, in one embodiment, are distributed over substantially all of the body-facing side of the sanitary napkin, with the exception of an unbonded window in a liquid receiving zone of the sanitary napkin. The topsheet with the acquisition component bonded thereto and the backsheet are preferably joined together along at least a portion of the periphery of the sanitary napkin. In other embodiments, especially in the case of thicker sanitary napkins, the bonded areas may be arranged similarly, but the bonds can be omitted from certain portions of the body-facing side of the sanitary napkin (for example, in regions at the ends of the main body portion of the sanitary napkin).

The attachment of the topsheet and acquisition component is believed to accomplish the objects set forth above, among others. The fusion of the faces of the topsheet and the acquisition component maintains these components in an attached condition, even under prolonged use. The sustained attachment also facilitates absorption of liquids into the underlying layers by maintaining an underlying absorbent layer in constant contact with the apertured film topsheet. The unbonded window provides a structure that does not interfere with the acquisition of liquids into the underlying layers.

DETAILED DESCRIPTION OF THE INVENTION

The present invention relates to absorbent articles such as sanitary napkins, panty liners, incontinence devices, diapers, and the like that have components that are bonded for improved integrity and have an unbonded window on their body-facing side for improved acquisition.

Figure 1:
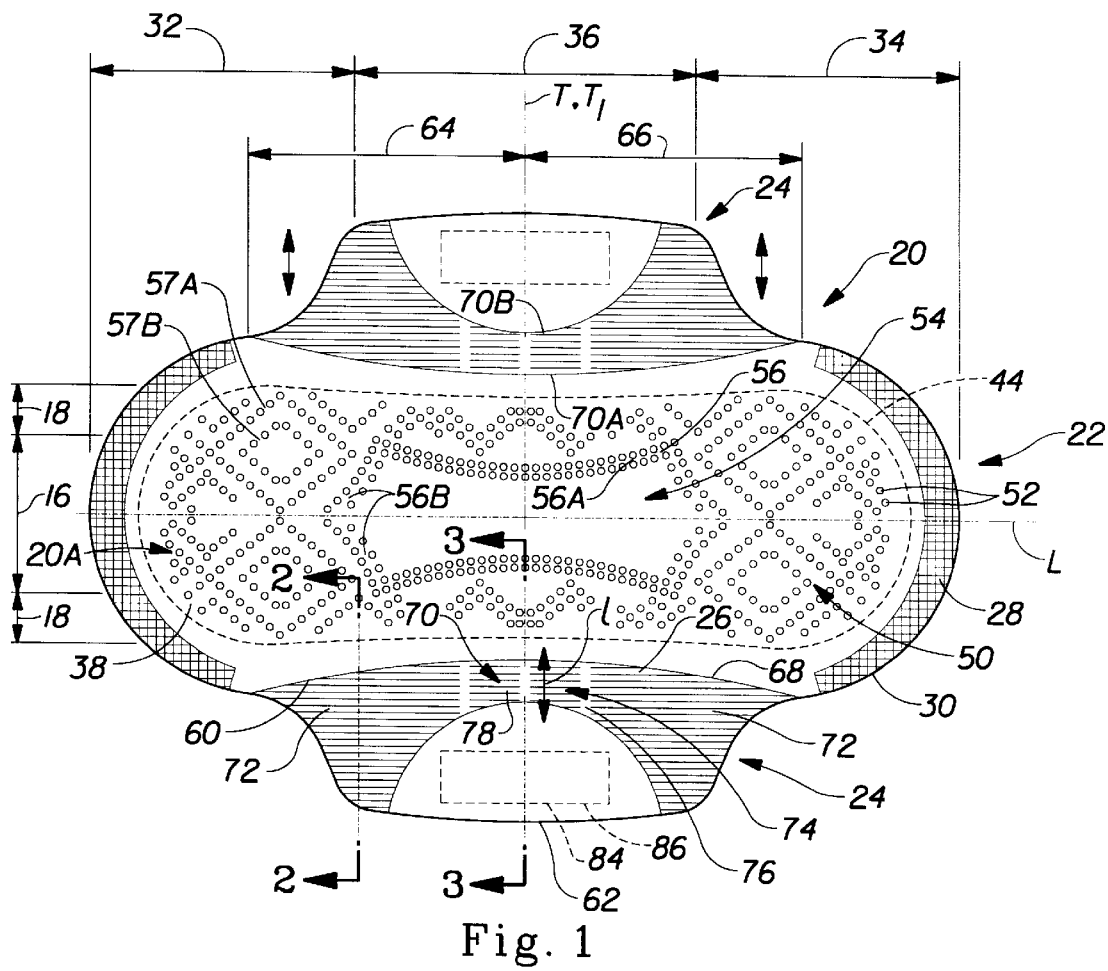
FIG. 1 is a top plan view of a preferred sanitary napkin embodiment of the present invention.

A preferred embodiment of a sanitary napkin 20 of the present invention is shown in FIG. 1. As shown in FIG. 1, the sanitary napkin 20 preferably comprises an absorbent means (or "main body portion") 22, and two optional flaps 24. The sanitary napkin 20 has two surfaces, a body-facing surface or "body surface" 20A and a garment surface 20B. The sanitary napkin 20 is shown in FIG. 1 as viewed from its body surface 20A (the latter being shown in FIG. 2). The body surface 20A is intended to be worn adjacent to the wearer's body. The garment surface 20B is intended to be placed adjacent to the wearer's undergarments when the sanitary napkin 20 is worn.

The sanitary napkin 20 has two centerlines, a principal longitudinal centerline L and a principal transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

FIG. 1 shows that the main body portion 22 of the sanitary napkin 20 comprises the portion of the sanitary napkin without the flaps 24. The main body portion 22 has two spaced apart longitudinal edges 26, two spaced apart transverse or end edges (or "ends") 28, which together form the periphery 30 of the main body portion. The main body portion 22 also has two end regions, which are designated first end region 32 and second end region 34. A central region 36 is disposed between the end regions 32 and 34. The end regions 32 and 34 extend outwardly in the longitudinal direction from the edges of the central region 36 about ⅛ to about ⅓ of the length of the main body portion. A detailed description of the characteristics of a central region and two end regions for a sanitary napkin is contained in U.S. Pat. No. 4,690,680 issued to Higgins on Sep. 1, 1987. The sanitary napkin 20 has a longitudinal central region 16 disposed along the length of at least a portion of the principal longitudinal centerline L, and longitudinal side regions 18 transversely outboard of the longitudinal central region 16.

The main body portion 22 of the sanitary napkin 20 can be of any thickness, including relatively thick, intermediate thickness, relatively thin, or even very thin (or "ultra thin"). An "ultra-thin" sanitary napkin 20 as described in U.S. Pat. Nos. 4,950,264 and 5,009,653 issued to Osborn preferably has a caliper of less than about 3 millimeters. The embodiment of the sanitary napkin 20 shown in FIGS. 1–3 of the drawings is intended to be an example of an ultra-thin sanitary napkin. The main body portion 22 of the sanitary napkin 20 may also be relatively flexible, so that it is comfortable for the wearer. It should, however, be understood that the sanitary napkins shown are merely two examples of embodiments, and that the present invention is not limited to absorbent articles of the type or having the specific configurations shown in the drawings.

Figure 2:
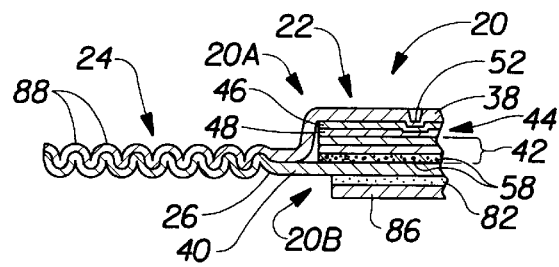
FIG. 2 is a lateral cross-sectional view taken along line 2—2 of the sanitary napkin shown in FIG. 1.

FIG. 2 shows the individual components of the main body portion 22 of the sanitary napkin 20 of the present invention. The main body portion 22 of the sanitary napkin preferably comprises at least four primary components. These include a liquid pervious topsheet 38, a liquid impervious backsheet 40, an absorbent core 42 positioned between the topsheet 38 and the backsheet 40, and at least one acquisition component 44. The acquisition component 44 may either be a separate component positioned between the topsheet 38 and the absorbent core 42, or it may comprise part of a composite topsheet or part of the absorbent core 42. The components of the sanitary napkin 20 may be comprised of any suitable materials that are capable of being bonded in the manner described herein. The topsheet 38 is a liquid pervious component that permits liquids (e.g., menses and/or urine) to readily penetrate through its thickness. The topsheet 38 is preferably as compliant, soft feeling, and non-irritating to the wearer's skin as possible. A suitable topsheet 38 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised at least partially of natural fibers (e.g., wood or cotton fibers), synthetic fibers (e.g., polymeric fibers such as polyester, polypropylene, or polyethylene fibers) or from a combination of natural and synthetic fibers.

A preferred type of topsheet comprises an apertured formed film. Apertured formed films are preferred for the topsheet because they are pervious to body exudates and, if properly apertured, have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; U.S. Pat. No. 4,637,819 entitled "Macroscopically Expanded Three-Dimensional Polymeric Web for Transmitting Both Dynamically Deposited and Statically Contacted Fluids From One Surface to the Other", which issued to Ouellette, et al. on Jan. 20, 1987; U.S. Pat. No. 4,780,352 entitled "Covering Structure For Absorbent Hygienic Sanitary Products, and an Absorbent Product Having Such A Covering", which issued to Palumbo on Oct. 25, 1988; U.S. Pat. No. 5,006,394 "Multilayer Polymeric Film" issued to Baird on Apr. 9, 1991; and U.S. patent application Ser. No. 08/442,935 entitled "Fluid Transport Webs Exhibiting Surface Energy Gradients" filed in the name of Ouellette, et al. on May 31, 1995 (PCT Publication WO 96/00548, published Jan. 11, 1996).

The terms "apertures" and "apertured" may include holes and/or slits which create passageways though the film layer from one surface to the other. The apertures can all be of the same size and shape, or they may be of different sizes and shapes. The apertures may be localized or they may extend across the entire surface of the film 38. When the aperturing is localized, it may be in the form of a longitudinal central portion or strip which separates two longitudinal side portions of the film which are not apertured. In addition, the entire topsheet can be made from a film or the longitudinal central portion can be made from a film and the longitudinal side portions can be made from another material such as a fibrous nonwoven web.

The apertured film 38 can be made of a number of suitable materials. Suitable polymers from which to form the apertured film 38 include any material which can be formed into a film including, but not limited to, polyolefins and polyacrylates, as well as copolymers and blends thereof Specific polymers include, but are not limited to, polyethylene (PE), low density polyethylene (LDPE), linear low density polyethylene (LLDPE) and ethylene vinyl acetate (EVA).

Typically the apertured film 38 will have a thickness between about 0.025 and about 1.0 millimeters and a percent open area due to the aperturing of between about 10 and about 40% based upon the surface area of the apertured film 38. Percent open area is calculated by specifying a unit area, calculating the surface area of all open areas within the specified unit area, dividing this total open area by the total surface within the specific unit area and then multiplying the quotient by 100 to yield percent open area. The size and number of apertures can be varied depending upon the viscosity and other properties of the body fluid being transported through the apertured film 38.

In preferred embodiments of the present invention, the body surface of the topsheet 38 is hydrophilic so that liquids will be transferred through the topsheet more readily. This diminishes the likelihood that menstrual fluid will flow off the topsheet rather than flowing into and being absorbed by the absorbent core. The body surface of the topsheet 38 can be made hydrophilic by treating it with a surfactant. Suitable methods of treating a topsheet with a surfactant are described in U.S. Pat. No. 4,950,254 issued to Osborn.

In a preferred embodiment, the topsheet 38 comprises an apertured formed film made in accordance with U.S. Pat. No. 4,342,314 issued to Radel, et al. and U.S. Pat. No. 4,463,045 issued to Ahr, et al., which is marketed on sanitary napkins as the DRI-WEAVE topsheet by The Procter & Gamble Company of Cincinnati, Ohio. Such an apertured film is preferably obtained as product No. X-5652 from Tredegar Film Products of Terre Haute, Ind. In this preferred embodiment, during manufacture the resin used to form the apertured film is preferably provided with a surfactant incorporated therein.

The acquisition component (or "acquisition layer") 44 lies beneath the topsheet 38. The terms "layer" or "web", as used herein, include but are not limited to single unfolded sheets, folded sheets, strips of material, loose or bonded fibers, multiple layers or laminates of material, or other combinations of such materials. These two terms are thus, not limited to single unfolded layers or sheets of material. The acquisition component 44 may provide void volume beneath the topsheet 38 to increase the ability of the sanitary napkin to draw liquids through the topsheet 38. In the preferred embodiment described herein, the acquisition component 44 preferably provides resiliency to lateral compressive forces so that the sanitary napkin 20 has improved resistance to bunching. The acquisition component 44 may have an effective average pore size that is equal to that of the topsheet 38, or less than that of the topsheet.

The acquisition component 44 should be liquid permeable. The acquisition component 44 is also preferably compliant, soft feeling, and non-irritating to the user's skin. The acquisition component 44 has a body-facing face (or side), and a garment-facing face. The acquisition component 44 may be of any suitable size and shape. In the embodiment shown in FIG. 1, the acquisition component 44 is in the shape of a race track with slightly concave side edges, as is the portion of the topsheet 38 that overlies the main body portion 22 of the sanitary napkin 20. The dimensions of the acquisition component 44, however, are preferably not as large as those of the topsheet 38. In other embodiments, such as in the case of thicker sanitary napkins, such as the one shown in FIG. 4, the acquisition component may be in the form of a piece of material that is smaller than the absorbent core 42.

The acquisition component 44 can be made from any materials suitable for the above purposes that are capable of having the topsheet 38 fused to them. The acquisition component 44 may, for example, be comprised of woven or nonwoven materials. The fibers or other components of these materials may be synthetic, or partially synthetic and partially natural. Suitable synthetic fibers include polyester, polypropylene, polyethylene, nylon, viscose rayon, or cellulose acetate fibers. Suitable natural fibers include cotton, cellulose, or other natural fibers. The acquisition component 44 may also be at least partially comprised of cross-linked cellulose fibers. The acquisition component 44, if nonwoven, can be made by a number of different processes. These include, but are not limited to: air laid, wet laid, meltblown, spunbonded, carded, thermally bonded, air-through bonded, powder bonded, latex bonded, solvent bonded, spunlaced, and combinations of the foregoing.

Suitable thermally bonded wet laid nonwoven webs (which may be referred to as "TBOWL" for brevity) are described in U.S. Pat. No. 5,549,589 entitled "Fluid Distribution Member for Absorbent Articles Exhibiting High Suction and High Capacity" issued to Horney, et al. on Aug. 27, 1996.

In the embodiment shown in the drawings, the acquisition component 44 preferably comprises a laminate of two materials. The uppermost layer of this laminate (or "secondary topsheet") 46 preferably comprises an 19 g/yd$^2$ (22.5 g/m$^2$) spunbonded polypropylene nonwoven material referred to as product No. 065MLPV60U (or "P-9") obtained from Fiberweb, North America of Washougal, Wash. The uppermost layer preferably has a void volume of about 11.2 cc/g measured at 689 dynes per square centimeter (0.01 psi.), and an average pore size, measured using the Laplace/Washburn equation for capillary tension of between about 60 and about 70 microns.

The underlying layer of the laminate (or "tertiary topsheet") 48 preferably comprises a multi-bonded air laid material that is thermally bonded using powder bonding and latex bonding. In a preferred embodiment, this multi-bonded air laid material comprises about 77% cellulose fibers, about 20% powder binder, and about 3% latex coating (1.5% sprayed on each side of the web) and has a basis weight of about 50 g/yd$^2$ (about 60 g/m$^2$). (Unless otherwise stated, all percentages herein are by weight.) Such a multi-bonded air laid material is preferably obtained as product No. 90830X312 from Merfin Hygienic Products, Ltd. of Delta, British Columbia, Canada.

These two layers are preferably laminated together by depositing the multi-bonded air laid material on the spunbonded polypropylene nonwoven material. The spunbonded material is used as a process aid or carrier web in the process of forming this laminate. The laminate preferably has a caliper of about 1.2 mm measured at a pressure of 68.9 Pascals, and a void volume of about 13.6 cc/g measured at 689 dynes per square centimeter. The acquisition component 44 is preferably hydrophilic. The acquisition component 44 may be more hydrophilic than the absorbent core, or it can have the same hydrophilicity as the absorbent core. If desired, the acquisition component 44 can be treated with a surface active agent to provide make it more hydrophilic. Preferably, it has the same hydrophilicity as the absorbent core.

In alternative embodiments, the spunbonded polypropylene nonwoven material may have a greater or a lower basis weight, or it may be replaced by an air laid tissue, a wet laid tissue, or any of the materials described above. If a wet laid tissue is used instead of a polypropylene nonwoven material, the orientation of the laminate is preferably reversed so that in the finished product, the multi-bonded air laid nonwoven material lies above the wet laid tissue layer. In the case of thicker sanitary napkins, any of the acquisition components described above can be used. Additionally, in one preferred thicker sanitary napkin embodiment, a low density latex bonded air laid material can be used as the entire acquisition component (that is, no tertiary topsheet is required). A low density latex bonded air laid material suitable for this purpose is a material having a basis weight of about 80 g/m$^2$ known as product No. FG413MHB, which is obtained from Walkisoft, USA of Mt. Holly, N.C.

The topsheet 38 is generally described herein as being fused to the acquisition component 44. This has been done for simplicity of description. (It is easier to discuss one preferred embodiment than it is to simultaneously describe all possible embodiments.) The topsheet 38 may be fused to one or more other underlying components. In the broadest sense, the topsheet comprises a first component that is fused to an underlying second component. The second component may be a separate component. Alternatively, the second component could be part of another component, such as part of the topsheet, part of the core, or part of some other component. In still other alternative embodiments, the acquisition component 44 may be omitted entirely. In embodiments where the acquisition component 44 is an integral layer of the core 42 or omitted entirely, the topsheet 38 may be considered to be fused to part of the absorbent core 42. In embodiments without an acquisition component 44, the absorbent core 42 can be comprised of at least some types of fibers (preferably synthetic fibers) that the topsheet 38 can be fused to. A sufficient amount of these fibers are preferably located near the body-facing surface of the absorbent core 42 to facilitate the fusion. Alternatively, if the absorbent core (or other underlying component) comprises powder binder, the topsheet 38 can be fused to the powder binder in the absorbent core 42 (or such underlying component).

In the preferred embodiment shown in the drawings, the acquisition component 44 is preferably joined to the apertured film topsheet 38 by fusion bonding the faces of the apertured film 38 and acquisition component, laminate 44. These components are bonded across a region of their surfaces that forms a "bonded region" 50 on the body-facing side 20A of the sanitary napkin 20.

The topsheet 38 and the laminate 44 are preferably bonded at a plurality of discrete bonded areas (or "bonds") 52. (However, it is also within the scope of the present invention for one or more of the individual bonds 52 to contact each other so that they are not spaced apart and discrete.) In the embodiment shown in FIG. 1, the bonded areas 52 are preferably spaced apart and distributed over the body-facing side 20A of the sanitary napkin 20, with the exception of a portion thereof that defines an unbonded window 54 in a liquid receiving zone of the sanitary napkin.

The discrete bonded areas prefer ably comprise fusion bonds 52. The fusion can be accomplished by heat and/or pressure bonds, ultrasonic bonds, dynamic mechanical bonds, and the like. Pressure can be applied in any suitable manner, such as by moving the components to be bonded between counter-rotating rolls, placing the materials on an anvil and forcing a platen down on the materials, applying vacuum pressure, and the like. Suitable means that can be adapted for use in fusing the topsheet 38 to the acquisition component 44 are described in at least some of the following patents: U.S. Pat. No. 4,430,148 Schaefer; U.S. Pat. No. 4,515,595 Kievit, et al.; U.S. Pat. No. 4,531,999 Persson, et al.; U.S. Pat. Nos. 4,710,189 and 4,808,252 issued to Lash; U.S. Pat. No. 4,823,783 Willhite, Jr., et al.; and U.S. Pat. Nos. 4,854,984 and 4,919,756 issued to Ball, et al.; and in allowed U.S. patent application Ser. No. 07/944,764 filed in the name of Cree, et al. on Sep. 14, 1992, the parent application which published Jun. 24, 1993 as PCT Publication No. WO 93/11725.

Figure 4:
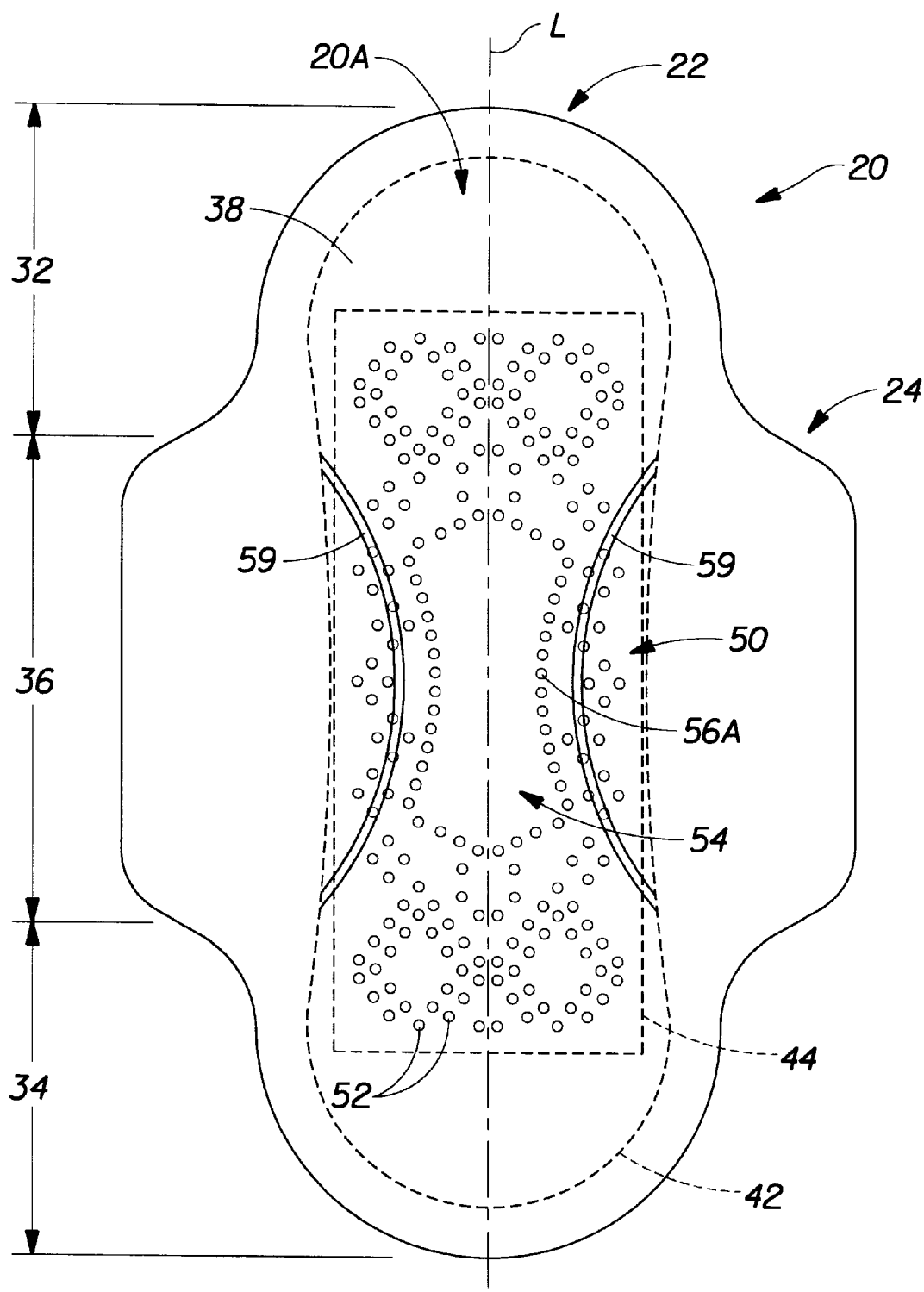
FIG. 4 is a top plan view of the topsheet of a thicker sanitary napkin showing a preferred bonding pattern thereon.

The fusion bonding preferably comprises a plurality of individual fusion bonds 52 that are arranged in a pattern. The bonds 52 can be arranged in many different patterns. FIGS. 1 and 4 show two particularly preferred bonding patterns. The individual bonds 52 that make up the pattern can be of any plan view shape. For instance, the bonds 52 can be in the form of straight or curved lines, geometric shapes such as circles, squares, rectangles, diamonds, and the like, or irregular shapes. In this embodiment, the fusion bonds 52 comprise a plurality of circular bonds.

The fusion bond s 52 may be of any suitable size, and may be distributed across the body-facing side 20A of the sanitary napkin in a range of suitable densities. The fusion bonds 52 preferably have a diameter that is greater than about 1 mm and ranges up to less than about 3 mm. In the sanitary napkins 20 shown in FIGS. 1 and 4, the fusion bonds are preferably about 1.5–2.0 mm in diameter. Providing fusion bonds within this range of sizes is preferred, especially with the DRI-WEAVE apertured film topsheet material. Providing fusion bonds 52 with smaller diameters creates manufacturing difficulties. In particular, difficulties are encountered because application of the pressure necessary to produce a bond by an element having a surface area less than about 1 mm in diameter will tend to perforate the apertured film topsheet material. Providing fusion bonds 52 with diameters greater than or equal to 3 mm in diameter has been found to negatively impact the consumer acceptance of the apertured film topsheet material. The apertured film is designed to allow liquids to pass through in one direction only. Providing bonds having such a larger size results in an increased belief that there will be a tendency for liquids to be "squeezed out" under pressure and pass back through the bonds and rewet the wearer's skin.

The edges of the fusion bonds 52 are preferably spaced more than about 0.5 mm apart in all directions. Closer bonds spacings have also been found to have a tendency to collapse the structure of the apertured film, which leads to higher rewet. The fusion bonds 52 are preferably distributed in a density that not only enhances the performance of the sanitary napkin, but also enhances the user's perception of the softness of the sanitary napkin and its absorbency. A bond density of between about 15–80 bonds per 9 $cm^2$ (including the area of the open window) is especially preferred for these purposes. Lower bond densities will tend to leave users with a perception of lower absorbency. Higher bond densities will tend to negatively impact absorbency.

The bond density need not be uniform over the entire surface of the sanitary napkin. For example, it will be appreciated from viewing FIGS. 1 and 4 that there will be areas on the surface of the sanitary napkin such as in the closed geometric figure (described below) surrounding the unbonded window 54 that will have bond densities at the higher end of this range, and other areas that will have bond densities at the lower end of this range. The fusion bonds 52 preferably cover between about 5% to about 15%, and more preferably about 8% to about 12% of the area on the surface of the sanitary napkin 20 that overlies the largest of the underlying absorbent layers.

In the embodiment shown in FIG. 1, the circular bonds 52 are arranged in a pattern that is preferably distributed over substantially the entire body surface 20A of the main body portion of the sanitary napkin, with the exception of the unbonded window 54 in the liquid receiving zone of the sanitary napkin. In the embodiment of a thicker sanitary napkin shown in FIG. 4, the bonds 52 may only be distributed over substantially all of that part of the main body portion 22 of the sanitary napkin 20 that overlies the acquisition component 44 (which is in the form of a rectangular patch), with the exception of the unbonded window 54 in the liquid receiving zone of the sanitary napkin.

The liquid receiving zone is the portion of the sanitary napkin that lies under the perineal area of the wearer. Preferably, the area of the unbonded window 54 is at least as large as, or larger than the perineal area of the wearer. Preferably, this area is greater than about 1 centimeter wide in the transverse direction and greater than about 5 centimeters long. The size of the unbonded window 54, however, is preferably not so large that the apertured film 38 is capable of appreciably separating from contact with the underlying acquisition component 44 in the area of the unbonded window 54 due to the lack of bonding therein. In the sanitary napkin 20 shown in FIG. 1, the unbonded window 54 is preferably centered about the longitudinal and transverse centerlines. However, in other embodiments, particularly ones in which the sanitary napkin is asymmetrically-shaped about the transverse centerline, the unbonded window 54 may be offset forwardly or rearwardly relative to the transverse centerline.

In the preferred embodiment shown in FIG. 1, the unbonded window 54 is defined by a plurality of fusion bonds 52 arranged in the configuration of a closed geometric FIG. 56. The closed geometric FIG. 56 is formed by a plurality of fusion bonds 52 arranged in a number of opposed, concave inwardly-oriented curvilinear lines around the unbonded window 54. The width or transverse dimension of this figure is preferably about 0.75 inches (about 1.9 cm) at its narrowest point. The length or longitudinal dimension of this figure is preferably about 3.5 inches (about 8.9 cm) as measured along the longitudinal centerline of the sanitary napkin 20.

The curvilinear lines forming the closed geometric figure preferably include a pair of longitudinally-oriented concave lines 56A. The longitudinally-oriented concave lines 56A preferably each comprise two rows of bonds where the bonds 52 in adjacent rows are arranged in a side-by-side fashion. These bonds 52 are preferably relatively closely spaced. These bonds 52 may, if desired, be designed to wick liquids in the longitudinal direction and provide a barrier to the flow of exudates in the transverse direction, particularly menses, so that menses will not approach the longitudinal side edges 26 of the sanitary napkin 20. The ends of the closed geometric figure that surrounds the unbonded window 54 are preferably formed by curvilinear lines 56B that form cusp-shaped figures. The intersection of the two arcs comprising the cusp-shaped figures lies along the longitudinal centerline of the sanitary napkin. These curvilinear lines 56B forming the cusp-shaped figures preferably also comprise roughly two rows of bonds, but these bonds are not exactly in a side-by-side pattern.

There are also bonds 52 located longitudinally and laterally outboard of the closed geometric FIG. 56. The fusion bonding preferably surrounds the unbonded window 54. The fusion bonds 52 are preferably located in the first end region 32, the second end region 34, and in longitudinal side regions 18 of the sanitary napkin 20. In the embodiment shown in FIG. 1, the fusion bonds 52 outside the unbonded window 54 are preferably distributed over substantially all of the body-facing side 20A of the main body portion 24 of the sanitary napkin that is inboard of any perimeter seal. These latter bonds 52 can also be arranged in a number of suitable patterns. Preferably, the bonding forms a "quilted pattern". More specifically, the bonds 52 are preferably arranged in a pattern that comprises a plurality of circular bonds arranged in a diamond-shaped FIG. 57A. The bonds that form the diamond-shaped FIG. 57A preferably enclose a plurality of bonds that also form a FIG. 57B. This enclosed FIG. 57B may range from a modified (or rounded) diamond shape to an oval shape. In the longitudinal side regions 18, only a portion of the diamond-shaped figures are present due to space constraints. For processing reasons, most of the bonds in the quilted pattern are preferably spaced apart in the longitudinal direction a distance that is equal to the radius of the bonds multiplied by the square root of three.

The acquisition component 44 can also be at least partially joined to the topsheet 38 by adhesives. If adhesives are used, the adhesives can be distributed across the entire interface between the topsheet 38 and the acquisition component 44. Preferably, however, the adhesives are not applied between these two components in the region of the unbonded window 54. Any suitable adhesives can be used for this purpose, with wet strength adhesives being preferred. Wet strength adhesives are those that retain their ability to bond in the presence of liquids. Suitable wet strength adhesives are described in U.S. Pat. No. 5,460,622 issued to Dragoo, et al. on Oct. 24, 1995.

If adhesives are used, they should not interfere with the transfer of liquids from the topsheet to the underlying acquisition layer or other underlying layers. The adhesives can be applied in a uniform continuous layer like meltblown fibers of adhesive, or a patterned layer, an array of separate lines, spirals, or spots of adhesive. The adhesive attachment means preferably comprises an open pattern network of filaments of adhesive as is disclosed i n U.S. Pat. No. 4,573,986 issued to Minetola, et al. on Mar. 4, 1986, or an open pattern network of filaments comprising several lines of adhesive filaments swirled into a spiral pattern as illustrated by the apparatus and method shown in: U.S. Pat. No. 3,911,173 issued to Sprague, Jr. on Oct. 7. 1975; U.S. Pat. No. 4,785,996 issued to Ziecker, et al. on Nov. 22, 1978; and U.S. Pat. No. 4,842,666 issued to Werenicz on Jun. 27, 1989.

The bonding of the acquisition component 44 to the underside of the topsheet 38 over substantially the entire surface of the body-facing side 20A provides several advantages. The bonding of the acquisition component 44 to the topsheet maintains an absorbent component in constant contact with the topsheet for improved acquistion. It also prevents the topsheet from separating from the underlying absorbent component and moving into the crevices in the wearer's body to cause discomfort.

The strength of the attachment between these layers is improved relative to the adhesively attached layers of currently marketed ALWAYS ULTRA sanitary napkins. Because of this improved attachment and the resilient nature of the materials comprising the acquisition layers, the sanitary napkin 20 is less subject to undesirable bunching in use and is, therefore, better able to cover a maximum area of the wearer's panties (that is, "area coverage" is improved). In the case of thicker sanitary napkins, the integrity of the sanitary napkin is greatly improved in comparison to thick sanitary napkins having airfelt absorbent cores under wet conditions. Typically, in sanitary napkins having airfelt cores, the airfelt will tend to collapse and slump and/or form balls or harder areas when wetted. In the case of thicker sanitary napkins provided with the features of the present invention, however, the force required to bunch the sanitary napkin is very close regardless of whether the sanitary napkin is wet or dry. This indicates that resistance to bunching is similar under wet and dry conditions.

In addition, the unbonded window 54 provides the body-facing side 20A of the sanitary napkin 20 with a region in the liquid receiving zone that is free of bonded areas to eliminate any interference with the acquisition of liquids caused by the presence of the bonds and to maximize the liquid handling capability of the sanitary napkin.

The absorbent core 42 lies under the acquisition component 44. The absorbent core 42 may be any absorbent means that is capable of absorbing or retaining liquids (e.g., menses and/or urine). The absorbent core 42 has a body-facing surface, a garment-facing surface, side edges, and end edges. The absorbent core 42 may be manufactured in a wide variety of sizes and shapes (e.g., rectangular, oval, hourglass, dog bone, asymmetric, etc.). In the preferred embodiment shown in FIG. 1 of the drawings, the absorbent core 42 is rectangular and is of a size that is slightly smaller than the periphery of the acquisition component 44. In the embodiment shown in FIG. 4, the absorbent core 42 is dog bone shaped, and is larger than the acquisition component 44.

The absorbent core 42 can be manufactured from a wide variety of liquid-absorbent materials commonly used in sanitary napkins and other absorbent articles. Examples of suitable absorbent materials include comminuted wood pulp which is generally referred to as airfelt; creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

In the preferred embodiment shown in the drawings, the absorbent core 42 preferably comprises a multi-bonded air laid material. In this preferred embodiment, this multi-bonded air laid material comprises about 50% to about 70% cellulose fibers, about 12% to about 20% bi-component fibers, about 10% to about 30% superabsorbent hydrogel-forming material (or absorbent gelling material) particles, and about 3% latex. The absorbent core 42 preferably has a caliper of about 1.5 mm under a pressure of 68.9 Pascals, and a basis weight of about 125 g/yd$^2$ (about 150 g/m$^2$), including the particles of absorbent gelling material (although much higher basis weight materials can also be used). Preferably, this multi-bonded air laid absorbent core 42 is formed by depositing three streams of cellulose and bi-component fibers, with absorbent gelling material particles 58 laid down with the last stream of fibers to form the bottom portion of the absorbent core. While the absorbent core 42 is shown as a laminate in FIGS. 2 and 3, in preferred embodiments, the fibers are blended together to form a single web. Such a multi-bonded air laid material is preferably obtained in roll form as product 915000X313 from Merfin Hygienic Products.

In alternative embodiments, the multi-bonded air laid material used for the absorbent core can be bonded using some material other than latex (such as starch or PVA, for example). In another alternative embodiment, the absorbent core can be formed as a laminate that preferably also has a basis weight of about 150 g/m² and comprises two (or more) layers of multi-bonded air laid nonwoven material with the particles of absorbent gelling material therebetween. Suitable laminate absorbent core structures are described generally in U.S. Pat. Nos. 4,950,264 and 5,009,653 issued to Osborn, U.S. Pat. No. 5,460,623 issued to Emenaker, et al. Another suitable absorbent core is described in U.S. patent application Ser. No. 08/122,114, entitled "Sanitary Napkin Having Core Predisposed To A Convex Upward Configuration", filed in the name of Hines, et al. on Sep. 16, 1993 (PCT Publication No. WO 95/07674, published Mar. 23, 1995).

In the above embodiments, or in other alternative embodiments, the absorbent core 42 can be provided with a feature to further improve its flexibility. Such a feature could include, but is not limited to one or more slits, perforations, embossments, or score lines in the absorbent core 42 or acquisition component 44. This type of feature is preferably arranged to improve flexibility about the principal longitudinal centerline of the sanitary napkin. The slits, perforations, embossments, or score lines can be in any suitable configuration. Suitable configurations include, but are not limited to straight or curved lines, slits, dots, V-shaped patterns, W-shaped patterns, or the like. The slits, perforations, embossments, or score lines, or any combination thereof can be provided in any of the layers of the laminate absorbent cores described above. One example of a feature that will improve the flexibility of the absorbent core 42 is a score line in the absorbent core that runs along the principal longitudinal centerline of the sanitary napkin.

In the case of thicker sanitary napkins, the absorbent core 42 is preferably comprised of airfelt. Suitable absorbent cores for thicker sanitary napkins are described in U.S. Pat. No. 5,234,422 issued to Sneller, et al. In a preferred embodiment, the topsheet 38, acquisition component 44, and absorbent core 42 can be provided with embossed channels as shown in the Sneller, et al. patent. As shown in FIG. 4, if such embossed channels 59 are used, they preferably lie laterally outside of the longitudinally-oriented concave lines 56A defining the sides of the unbonded window 54.

The backsheet 40 prevents the exudates absorbed and contained in the absorbent core 42 from wetting articles which contact the sanitary napkin 20 such as pants, pajamas and undergarments. The backsheet 40 is preferably resistant to the flow of liquids, and more preferably is impervious to liquids (e.g., menses and/or urine). The backsheet 40 is preferably manufactured from a flexible material. As used herein, the term "flexible" refers to materials which are compliant and will readily conform to the general shape and contours of the human body. The backsheet 40 may comprise a woven or nonwoven material, polymeric films such as thermoplastic films of polyethylene or polypropylene, or composite materials such as a film-coated nonwoven material. Preferably, the backsheet 40 is a polyethylene film having a thickness of from about 0.012 mm (0.5 mil) to about 0.051 mm (2.0 mils). The backsheet 40 may be embossed and/or matte finished to provide a more clothlike appearance. Further, the backsheet 40 may permit vapors to escape from the absorbent core 42 (i.e., breathable) while still preventing exudates from passing through the backsheet 40. A suitable backsheet material is obtained as product No. 18-1401 from the Clopay Corporation of Cincinnati, Ohio. A suitable breathable backsheet material is a laminate of an apertured film such as that described in U.S. Pat. No. 3,929,135 issued to Thompson which is inverted so that the smaller openings of the tapered capillaries face the absorbent core 42 which is adhesively laminated to a microporous film such as that described in Exxon's U.S. Pat. No. 4,777,073.

Figure 3:
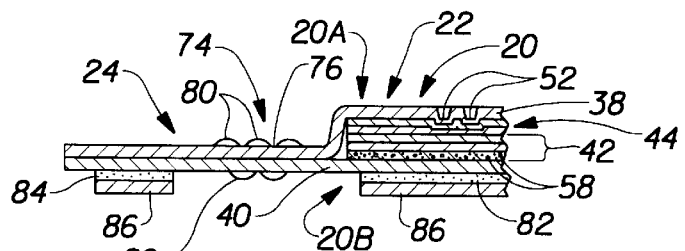
FIG. 3 is a lateral cross-sectional view taken along line 3—3 of FIG. 1 through the center portion of one of the flaps.

The topsheet 38, the acquisition component 44, the backsheet 40, and the absorbent core 42 may be assembled in a variety of configurations known in the art (including layered or "sandwich" configurations and wrapped or "tube" configurations). FIGS. 1–3 show a preferred embodiment of the sanitary napkin 20 assembled in a sandwich construction. In FIGS. 1–3, the topsheet 38 and the backsheet 40 have length and width dimensions generally larger than those of the absorbent core 42. The topsheet 38 and the backsheet 40 extend beyond the edges of the absorbent core 42 to form portions of the periphery 30. The garment-facing side of the topsheet 38 is preferably joined to the body-facing side of the acquisition component 44 as described above. The acquisition component 44 may be joined to the absorbent core 42, if desired. If these components are joined, they can be joined in any of the manners described herein for joining the topsheet 38 to the acquisition component 44. However, in the embodiment shown in the drawings, the acquisition component 44 is not directly joined to the absorbent core 42. The backsheet 40 is preferably joined to the garment-facing side of the absorbent core by adhesives.

The portions of the topsheet 38 and backsheet 40 that extend beyond the edges of the absorbent core 42 and the acquisition component 44 are preferably also joined to each other. These portions of the topsheet 38 and backsheet 40 can be joined in any suitable manner known in the art. The term "joined", as used in this specification, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. Preferably, in the embodiment shown, these portions of the topsheet 38 and backsheet 40 are joined using adhesives over substantially the entire portions that extend beyond the edges of the absorbent core 42 and a crimp seal at the end edges 28 of the main body portion where the topsheet 38 and backsheet 40 are densified by the application of pressure or heat and pressure.

The sanitary napkin 20 shown in FIGS. 1–3, as discussed above, comprises an optional pair of flaps 24 that are joined to the main body portion 22. The flaps 24 extend laterally outward beyond the longitudinal side edges 26 of the main body portion 22 from their proximal edges 60 to their distal edges (or "free end") 62. The flaps 24 extend outward from at least the central region 36 of the main body portion 22. As shown in FIG. 1, each flap 24 is divided into a front half 64, and a back half 66 by a flap transverse centerline $T_1$. The flap transverse centerline $T_1$ may coincide with the principal transverse centerline T of the sanitary napkin, but this is not absolutely required.

The flaps 24 can be joined to the main body portion 22 in any suitable manner. Preferably, in the embodiment shown in FIGS. 1–3, the flaps 24 are integral with the main body portion 22 (that is, the flaps 24 comprise integral extensions of the topsheet 38 and backsheet 40). In other alternative embodiments, the flaps 24 can comprise separate components that are joined to the main body portion 22. The flaps 24 are each joined to (or associated with) main body portion 22 along a juncture. This is typically a longitudinally-oriented (or "longitudinal") juncture, such as lines of juncture 68. As used herein, the terms "juncture" (or "line of juncture") refer to regions where the flaps 24 extend from or are joined to the main body portion 22. The line of juncture 68 in the embodiment illustrated in the drawings can be considered to be defined by concave inwardly-oriented regions or lines.

The flaps 24 can be in any suitable configuration. Suitable flaps are described in Reexamined U.S. Pat. No. B1 4,589,876 entitled "Sanitary Napkin", issued to Van Tilburg, Certificate of Reexamination issued Apr. 27, 1993; U.S. Pat. No. 4,687,478 entitled "Shaped Sanitary Napkin With Flaps", which issued to Van Tilburg on Aug. 18, 1987; U.S. Pat. No. 5,389,094 entitled "Absorbent Article Having Flaps and Zones of Differential Extensibility" issued to Lavash, et al. on Feb. 14, 1995; U.S. Pat. No. 5,558,663 entitled "Absorbent Article Having Undergarment Covering Components With Zones of Extensibility" issued to Weinberger, et al. on Sep. 24, 1996 (which describes an alternative to flaps that are applied by the wearer); and in International Patent Application Serial No. PCT US 96/15957 entitled "Absorbent Article Having Flaps With Step Configuration and Zones of Extensibility" filed on Oct. 3, 1996, in the name of Lash, et al.

The sanitary napkin 20 shown in FIGS. 1–3 preferably has a deformed region that forms a hinge 70 between the main body portion 22 and at least a portion of the flaps 24. The sanitary napkin 20 preferably also has at least one zone of extensibility (or "zone of differential extensibility") 72 for relieving the stresses on the flaps 24 when they are folded around a panty crotch. These features are each described below.

In the sanitary napkin shown in FIGS. 1–3, the hinge 70 comprises a generally longitudinally-oriented, mechanically-deformed region. The hinge 70 provides a region of the sanitary napkin 20 with increased flexibility to create preferred bending axes for the flaps 24 to bend or fold about. The hinge 70 is preferably located in a region along the juncture 68 of the flaps 24 with the main body portion 22. The hinge 70 can extend along the entire juncture 68 of the flaps with the main body portion, or along only a portion thereof. If the hinge 70 is only provided along a portion of the juncture 68, it is preferably provided in the region of the sanitary napkin 20 surrounding and including the flap transverse centerline $T_1$. The hinge 70 has a laterally inwardmost, or proximal, boundary 70A and an outermost, or distal, boundary 70B. In the embodiment shown in FIGS. 1–3, at least the inwardmost boundary 70A of the hinge 70 is preferably concave inwardly relative to the distal edge of the flaps 24.

The hinge 70 can be formed in any suitable manner that provides the desired region of the sanitary napkin with increased flexibility. Preferably, the hinge 70 is formed by mechanically deforming the desired regions of the sanitary napkin. It has been found that many processes suitable for providing regions of the sanitary napkin with extensibility are particularly suitable for providing regions of the sanitary napkin selected for the hinge 70 with enhanced flexibility. The hinge 70 can, for instance, be formed by a process which has been described as pre-corrugating (or "ring rolling"), or by a process that involves forming a strainable network in the desired portion of the sanitary napkin. Suitable methods for ring rolling are described in U.S. Pat. No. 4,107,364 issued to Sisson on Aug. 15, 1978, U.S. Pat. No. 5,143,679 issued to Gerald M. Weber, et al. on Sep. 1, 1992, U.S. Pat. No. 5,156,793 issued to Kenneth B. Buell, et al. on Oct. 20, 1992, and U.S. Pat. No. 5,167,897 issued to Gerald M. Weber, et al. on Dec. 1, 1992. Preferably, as shown in FIG. 1, the hinge 70 is provided by forming a strainable network region along the juncture 68 of the flaps 24 with the main body portion 22. The process for forming a strainable network region, and structures formed thereby are described in greater detail in U.S. Pat. No. 5,518,801 issued to Chappell, et al. on May 21, 1996.

The term "strainable network", as used herein, refers to an interconnected and interrelated group of regions which are able to be extended to some useful degree in a predetermined direction. The strainable network 74 comprises at least two distinct and dissimilar regions which are designated as first region 76 and second region 78. In the embodiment shown, the strainable network 74 includes a plurality of first regions 76 and a plurality of second regions 78. As shown in FIGS. 1–3, the first regions 76 are substantially planar regions. That is, the material within the first region 76 is in substantially the same condition before and after the formation of the strainable network 74. The second regions 78 include a plurality of continuous, interconnected, rib-like deformations 80 which extend alternately beyond the plane of both surfaces of the first region 76.

FIG. 1 shows that the flap material 24 having the strainable network 74 formed therein has a longitudinal centerline (or axis), 1. In the sanitary napkin embodiment shown in FIG. 1, the longitudinal centerline, 1, of the strainable network 74 is rectilinear and generally oriented in the transverse direction. In the sanitary napkin 20 shown in FIG. 1, the first regions 76 are substantially linear, extending continuously in a direction substantially parallel to the longitudinal axis 1 of the strainable network.

The hinge 70 is created by forming the strainable network 74 into the desired portion of the sanitary napkin 20. As used herein, the term "forming" refers to the creation of a desired structure or geometry upon a web material or laminate that will substantially retain the desired structure or geometry when it is not subjected to any externally applied elongations or forces. Suitable methods for forming a strainable network into a web material include, but are not limited to embossing by mating plates or rolls, thermoforming, high pressure hydraulic forming, and casting.

The depth and number of deformations 80 in the strainable network 74 can be varied to control the applied force or elongation required to extend the material in the hinge regions 70 of the sanitary napkin 20. In one embodiment, the deformations 80 may be formed by two rigid plates having a pattern of meshing teeth. The outer dimensions of the pattern of teeth covers a surface area of the plates that is about 7.9" by 1.6" (20 cm by 4 cm) for each flap. On one surface of each plate are a series of teeth which are substantially triangular in cross section and taper to a radiused vertex. The teeth in this embodiment preferably have a height of 3.175 mm, and are evenly spaced with the centerlines of the teeth spaced apart at 0.075" (1.9 mm) increments. On the "toothed" side of one plate, a series of grooves (preferably three grooves to construct the embodiment shown in FIG. 1) are cut which are parallel to each other and perpendicular to the evenly spaced teeth. These grooves correspond to the undeformed regions of the base material.

The preferred base material is placed between the plates in a hydraulic press having platens larger than the plates to evenly distribute pressure. The plates are compressed so that the teeth only partially engage (or mesh). Preferably, the plates are moved so that the teeth on the opposite plates are pressed toward each other about 80% of the distance toward full engagement (the point where the teeth would otherwise touch). Typically, in order to do this, when the base material comprises a laminate of apertured formed film and polyethylene backsheet material laminated together by adhesives that is described in conjunction with the embodiment shown in FIGS. 1–3, the plates will be compressed under a load of between about 25–70 psi. (about 1,750–4,900 g/cm$^2$). The formed web material is then removed from between the plates. In the embodiment shown in FIGS. 1–3, the formed web material is provided with about 75% extensibility.

The strainable network region 74 comprises alternating ridges and valleys that form a plurality of flexible bending axes for the flaps 24. This structure also provides the hinge 70 with a degree of extensibility. The extensibility allows the portions of the flaps 24 in the hinge region 70 to expand slightly in the transverse direction to better fold around the curved sides of the wearer's panty crotch. Providing the hinge 70 by forming strainable network regions in the sanitary napkin may also be preferred when it is desired to provide the formed regions with slightly more integrity so the flaps 24 will be less likely to droop excessively at the hinge 70 because the unformed first regions or less extensible bands 76 of the strainable network will serve like "beams" that tend to provide the flaps 24 with slightly more structural rigidity and better appearance.

The sanitary napkin also preferably has zones of extensibility 72 for relieving the stresses that develop in the flaps when they are folded down and under a wearer's undergarment. The terms "zone of extensibility" or "zone of differential extensibility", as used herein, refer to a portion of the sanitary napkin 20 which is capable of extending (and are preferably capable of extending a greater amount than surrounding portions of the sanitary napkin 20). The sanitary napkin 20 preferably has at least one zone of extensibility 72 for each flap 24, and more preferably has four zones of extensibility 72, one in each quarter of the sanitary napkin 20. Since the zones of differential extensibility 72 relieve stresses in the flaps, they may be referred to herein as a type of "stress relief means".

The sones of extensibility 72 can be extensible in any desired direction, or in more than one direction. However, the zones of extensibility 72 are preferably primarily extensible generally outward in the transverse direction. This is generally in the direction of the arrows shown in FIG. 1. As used herein, "generally in the transverse direction" means that the extensibility has a transverse component. All of the extension, however, need not be exactly parallel to the principal transverse centerline of the sanitary napkin. The extensibility, however, is preferably oriented more in the transverse direction than in the longitudinal direction. The zones of extensibility 72 can comprise any structure capable of extending in the transverse direction (or in any other direction desired). Suitable structures for the zones of extensibility are described in greater detail in U.S. Pat. No. 5,389,094 issued to Lavash, et al. on Feb. 14, 1995. In the embodiment shown in FIG. 1, the zones of extensibility 72 can either comprise ring rolled regions of the flaps or a network of corrugations without any less extensible bands therein. In either case, the zones of extensibility 72 preferably have corrugations with ridges 88 that are oriented generally in the longitudinal direction so that the zones of extensibility 72 will be extensible primarily in the transverse direction.

Preferably, as shown in FIG. 1, the hinge 70 is contiguous (that is, touching or connected throughout in an unbroken sequence) with the zones of extensibility 72. The hinge 70 and the preferred ring rolled zones of extensibility 72 are, thus, portions of a continuous composite deformed region. As shown in FIG. 1, the hinge 70 gradually transitions into portions of the sanitary napkin that comprise the zones of extensibility 72. The composite deformed region, thus, comprises continuous corrugations having ridges that are generally oriented in the longitudinal direction with a plurality of less extensible bands 76 in the center region adjacent the flap transverse centerline $T_1$.

The garment surface 20B of the sanitary napkin 20 may include, and preferably does include, fasteners for attaching the sanitary napkin to the wearer's undergarment. FIG. 2 shows the central pad fastener 82 which is adapted to secure the main body portion 22 of the sanitary napkin to the crotch region of an undergarment. Any types of fasteners known in the art, such as adhesive fasteners and mechanical fasteners can be used. Fasteners comprising adhesives have been found to work well for this purpose, with pressure-sensitive adhesives being preferred. In a preferred embodiment, the central pad fastener 82 comprises a pair of spaced apart longitudinally-oriented strips or zones of adhesive that are centered about the longitudinal centerline L.

The outer surface of the flaps 24, adjacent the distal edges 62 of the flaps, is preferably provided with a flap adhesive 84. The flap adhesive 84 is used to assist in maintaining the flaps 24 in position after they are wrapped around the edge of the crotch portion of the panty. Suitable adhesive fasteners are described in greater detail in U.S. Pat. No. 4,917,697. The flaps 24 can be maintained in position by attaching the flaps 24 to the undergarment, or to the opposing flap.

The fasteners used with the present invention are not limited to adhesive attachment means. Any type of fastener used in the art can be used for such purpose. For example, the sanitary napkin 20 could be secured to the wearer's undergarment by mechanical fasteners, such as VELCRO, or the fasteners described in U.S. Pat. No. 4,946,527 entitled "Pressure-Sensitive Adhesive Fastener and Method of Making the Same" issued to Battrell on Aug. 7, 1990, or U.S. Pat. No. 5,392,498 entitled "Non-Abrasive Skin Friendly Mechanical Fastening System" issued to Goulait, et al. on Feb. 28, 1995. For simplicity, however, the fasteners will be described in terms of adhesive attachment means.

The adhesive attachment means are respectively covered by removable release liners, central pad release liner and flap release liner, both designated 86. The pressure-sensitive adhesives should be covered with release liners 86 to keep the adhesives from sticking to extraneous surfaces prior to use. Suitable release liners are described in U.S. Pat. No. 4,917,697. A particularly preferred release liner which also serves as an individual package for wrapping the sanitary napkin is described in U.S. Pat. No. 4,556,146 issued to Swanson, et al.

Numerous other embodiments of the sanitary napkin 20 are possible. For example, the main body portion of the sanitary napkin can be provided in the form of a compound sanitary napkin that has its components bonded as described herein for improved integrity and acquisition. General descriptions of compound sanitary napkins are found in P&G's U.S. Pat. No. 4,425,130 entitled "Compound Sanitary Napkin" issued to DesMarais, et al. on Jan. 10, 1984, and in Statutory Invention Registration H1614 entitled "Body Fitting Compound Sanitary Napkin", published in the name of Mayer, et al. on Nov. 5, 1996. To form the compound sanitary napkin, a sanitary napkin such as that described herein can serve as the panty protector (or "base pad") and a tube of absorbent material wrapped by a topsheet (or "primary menstrual pad") can be placed on top of the sanitary napkin and attached thereto at the ends. The fusion bonding on the base pad is preferably distributed in the same manner as shown on the drawings herein. The attachment of the tube to the sanitary napkin is preferably achieved by fusion bonding extensions of the topsheet material at the ends of the tube to the base pad. In some preferred embodiments of such a compound sanitary napkin, there may also be attachment between the ends of the tube of absorbent material and the base pad. The tube of the compound sanitary napkin can be attached to the base pad between its ends by any suitable attachment means, such as by adhesives.

It is believed that the improved attachment between the topsheet and acquisition component in the base pad may have a particular advantage in the context of a compound sanitary napkin. Without wishing to be bound by any particular theory, it is believed that the improved attachment will result in a reduced tendency for the topsheet to separate from the underlying components along the longitudinal side regions of the sanitary napkin. This is believed to be particularly important on versions of a compound sanitary napkin having flaps. The fusion bonding ensures that the portion of the topsheet in the longitudinal side regions of the base pad will not move into contact with the wearer's body. This will reduce the tendency for the longitudinal side regions to be soiled by menses, and menses will instead proceed directly into the absorbent tube.

Other advantages from the bonding described herein are also possible. For example, when the sanitary napkin is provided with flaps, the portion of the topsheet and backsheet that are joined together to form the flaps of the sanitary napkin may be substantially free of adhesive between the parts of the same to leave a "glue-free window" in a portion of the flaps. A suitable sanitary napkin that can have a glue-free window in its flaps is described in European Patent Application EP 0 695 542 A1 entitled "Absorbent Article Having Undergarment Side Wrapping Elements", published in the name of Coles, et al. on Feb. 7, 1996. In such embodiments, the topsheet and backsheet are, however, preferably bonded to each other at least along the entire perimeter of the flaps and in any extensible portions of the flaps.

Providing a sanitary napkin having flaps with a glue-free window has the advantage of providing the flaps with increased flexibility in the area of the glue-free window. This is due to the absence of adhesive in this portion of the flaps and the fact that the portions of the topsheet and backsheet forming the flaps can fold independently of each other in the glue-free window. A potential disadvantage of the glue-free window, however, is that the topsheet may tend to billow or "blouse" and separate from the backsheet, particularly when it is folded around the sides of the wearer's undergarment. Without wishing to be bound by any particular theory, it is believed that the improved attachment described herein will better keep the topsheet attached to an underlying component and reduce such blousing. In this embodiment, and all of the other embodiments described herein, it is believed that the improved attachment between the topsheet and the underlying component(s) will result in menses being absorbed better and hidden from view (or "masked"), and will reduce the tendency for menses to "run off" the topsheet.

In addition, it is also possible to form a sanitary napkin (or other absorbent article) with a pattern of embossments with the characteristics of the bond areas on the sanitary napkin described above. Such an absorbent article may be less preferred, but it will provide the consumer benefits of increasing the wearer's confidence in the softness, absorbency, and reduction in rewet associated with the absorbent article.

The sanitary napkin 20 of the present invention is utilized by removing the release liners 86 and placing the sanitary napkin 20 in a panty. The main body portion 22 is placed in the crotch portion of the panty with one end of the main body portion 22 extending towards the front section of the panty and the other end towards the back section of the panty. The backsheet 40 is placed in contact with the inner surface of the center of the crotch portion of the panty. The central pad adhesive fastener 82 maintains main body portion 22 in position. The distal portions of the flaps 24 are folded around the side edges of the panty. The flap adhesives 84 secure the flaps 24 to the underside of the panty or to the opposing flap.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent article having a body-facing side, said absorbent article comprising:

a liquid pervious topsheet defining said body-facing side of said absorbent article;

a liquid impervious backsheet joined to said topsheet; and an underlying liquid pervious layer having a thickness, said underlying layer being positioned between said topsheet and said backsheet, wherein said body-facing side of said absorbent article has a bonded region and an unbonded window wherein said topsheet is fused to said underlying layer at a plurality of individual bonded areas that are located in said bonded region, and said unbonded window on said body-facing side is substantially free of bonded areas, and is surrounded by a closed geometric figure formed by a plurality of spaced apart bonds which is surrounded by said bonded region, wherein at least some of said bonds in said bonded region are arranged in a quilted pattern that comprises a plurality of bonds arranged in the pattern of a diamond and several bonds arranged in a pattern inside said diamond pattern, said bonded areas having a circular plan view shape with a diameter between about 1 mm and about 3 mm, and being distributed in a density of between about 2 and about 9 bonds per cm$^2$.

2. The absorbent article of claim 1 wherein said bonded areas have outer edges, and the outer edges of said bonded areas are spaced more than about 0.5 mm apart.

3. The absorbent article of claim 1 having a longitudinal centerline, wherein said unbonded window is centered about said longitudinal centerline.

4. The absorbent article of claim 1 wherein said bonds have a circular plan view shape.

5. The absorbent article of claim 4 wherein said bonds which form said closed geometric figure are arranged in a number of opposed, concave inwardly-oriented, curvilinear lines.

6. The absorbent article of claim 1 wherein said unbonded window is surrounded by a plurality of spaced apart bonds arranged in a quilted pattern that covers substantially all of that portion of said body-facing side of said absorbent article located in said bonded region.

7. The absorbent article of claim 6 wherein said bonds inside said diamond pattern are arranged in the configuration of a rounded shape within said diamond pattern.

8. The absorbent article of claim 7 wherein said pattern of bonds is a repeating pattern.

9. The absorbent article of claim 1 wherein said bonds comprise heat and pressure bonds.

10. The absorbent article of claim 1 wherein said bonds comprise ultrasonic bonds.

11. The absorbent article of claim 1 wherein said topsheet comprises an apertured thermoplastic film.

12. The absorbent article of claim 11 wherein said underlying liquid pervious layer comprises a spunbonded polypropylene nonwoven material.

13. The absorbent article of claim 11 wherein said underlying liquid pervious layer comprises at least one layer of multi-bonded air laid nonwoven material.

14. The absorbent article of claim 11 wherein said underlying layer comprises a laminate comprised of a spunbonded polypropylene nonwoven material and a multi-bonded air laid nonwoven material.

15. The absorbent article of claim 13 further comprising an absorbent core positioned between said liquid pervious layer and said backsheet wherein said absorbent core comprises at least one layer of multi-bonded air laid nonwoven material.

16. The absorbent article of claim 11 wherein said underlying liquid previous layer comprises a latex bonded air laid nonwoven material.

17. The absorbent article of claim 16 further comprising an airfelt absorbent core positioned between said liquid pervious layer and said backsheet.

18. A sanitary napkin having a body-facing side, and a longitudinal centerline, said sanitary napkin comprising:

a liquid pervious apertured thermoplastic film topsheet;

a liquid impervious backsheet joined to said topsheet;

a laminate acquisition component positioned between said topsheet and said backsheet, said acquisition component comprising a two layer nonwoven structure comprising a spunbonded polypropylene nonwoven material closest to said thermoplastic film and a multi-bonded air laid nonwoven material beneath said polypropylene nonwoven material, wherein said apertured film and said laminate acquisition component are bonded together by a plurality of fusion bonds;

an absorbent core positioned between said topsheet and said acquisition component, said absorbent core comprising a multi-bonded air laid nonwoven material comprising cellulose fibers, bi-component fibers, a latex binder, and a plurality of particles of superabsorbent hydrogel-forming material;

wherein said body-facing side of said sanitary napkin has a bonded region and an unbonded window wherein said topsheet is fused to said laminate acquisition material at individual bonded areas that are located in said bonded region and said unbonded window is substantially free of bonds, and is surrounded by said bonded region, said bonded areas having a circular plan view shape with a diameter between about 1 mm and about 3 mm, and being distributed in a density of between about 2 and about 9 bonds per cm$^2$.

19. A sanitary napkin having a body-facing side, a garment-facing side, and a longitudinal centerline, said sanitary napkin comprising:

a liquid pervious apertured thermoplastic film topsheet;

a liquid impervious backsheet joined to said topsheet;

an acquisition component positioned between said topsheet and said backsheet, said acquisition component comprising a latex bonded air laid nonwoven material;

an airfelt absorbent core positioned between said acquisition component and said backsheet;

wherein said body-facing side of said sanitary napkin has a bonded region and an unbonded window wherein said topsheet is fused to said acquisition component at individual bonded areas that are located in said bonded region and said unbonded window is substantially free of bonds, and is surrounded by a closed geometric figure formed by a plurality of spaced apart bonds which is surrounded by said bonded region, wherein at least some of said bonds in said bonded region are arranged in a quilted pattern that comprises a plurality of bonds arranged in the pattern of a diamond and several bonds arranged in a pattern inside said diamond pattern, said bonded areas having a circular plan view shape with a diameter between about 1 mm and about 3 mm, and being distributed in a density of between about 2 and about 9 bonds per cm$^2$.

20. An absorbent article having a body-facing side, said absorbent article comprising:

a liquid pervious topsheet defining said body-facing side of said absorbent article;

a liquid impervious backsheet joined to said topsheet; and an underlying liquid pervious layer having a thickness, said underlying layer being positioned between said topsheet and said backsheet, wherein said body-facing side of said absorbent article has a bonded region and an unbonded window wherein said topsheet is fused to said underlying layer at a plurality of individual bonded areas that are located in said bonded region, and said unbonded window on said body-facing side is substantially free of bonded areas, wherein said unbonded window is surrounded by a plurality of spaced apart bonds arranged in the shape of a closed geometric figure having opposed concave inwardly oriented curvilinear sides, and said bonds are distributed in a density of between about 2 and about 9 bonds per cm$^2$.

* * * * *